(12) United States Patent
Ehrensberger et al.

(10) Patent No.: US 9,616,142 B2
(45) Date of Patent: Apr. 11, 2017

(54) ELECTROCHEMICAL ERADICATION OF MICROBES ON SURFACES OF OBJECTS

(71) Applicants: The Research Foundation for The State University of New York, Amherst, NY (US); Syracuse University, Syracuse, NY (US)

(72) Inventors: Mark Ehrensberger, Amherst, NY (US); Anthony A. Campagnari, Hamburg, NY (US); Esther Takeuchi, East Amherst, NY (US); Nicole Luke-Marshall, Webster, NY (US); Jeremy Gilbert, Fayetteville, NY (US)

(73) Assignees: The Research Foundation for The State University of New York, Amherst, NY (US); Syracuse University, Syracuse, NY (US)

( * ) Notice: Subject to any disclaimer, the term of this patent is extended or adjusted under 35 U.S.C. 154(b) by 58 days.

(21) Appl. No.: 14/540,213

(22) Filed: Nov. 13, 2014

(65) Prior Publication Data

US 2015/0073491 A1    Mar. 12, 2015

Related U.S. Application Data

(63) Continuation of application No. 14/395,640, filed as application No. PCT/US2013/037637 on Apr. 22, 2013, application No. 14/540,213, which is a continuation-in-part of application No. 12/534,443, filed on Aug. 3, 2009, now Pat. No. 9,039,764.

(60) Provisional application No. 61/636,349, filed on Apr. 20, 2012.

(51) Int. Cl.
*A61L 2/03* (2006.01)
*A61F 2/30* (2006.01)
*A61F 2/48* (2006.01)

(52) U.S. Cl.
CPC ....... *A61L 2/03* (2013.01); *A61F 2/30* (2013.01); *A61F 2002/30677* (2013.01); *A61F 2002/482* (2013.01); *A61L 2202/24* (2013.01)

(58) Field of Classification Search
CPC ............ A61L 2/03; A61L 2/0011; A61F 2/30
See application file for complete search history.

(56) References Cited

U.S. PATENT DOCUMENTS

| | | | |
|---|---|---|---|
| 4,027,392 A | 6/1977 | Sawyer et al. | |
| 4,540,477 A * | 9/1985 | Lin | B22F 1/004 204/242 |
| 4,735,693 A * | 4/1988 | Asai | G01N 27/48 205/768 |

(Continued)

*Primary Examiner* — Regina M Yoo
(74) *Attorney, Agent, or Firm* — Hodgson Russ LLP

(57) ABSTRACT

The invention describes a method of reducing or preventing the growth of microbes on the surface of an object, wherein the object is of such material that it can act as a working electrode. The method comprises the steps of providing a counter electrode, and a reference electrode. The object is used as the working electrode. Electrical current is passed through the working and counter electrodes. The current through the counter electrode is varied such that the electric potential of the working electrode is constant relative to the electric potential of the reference electrode. Also described is an apparatus for reducing or preventing microbes on an object using a potentiostatic device.

16 Claims, 14 Drawing Sheets

(56) References Cited

U.S. PATENT DOCUMENTS

| | | | | |
|---|---|---|---|---|
| 4,839,017 | A | * | 6/1989 | Taniguchi ............ C08G 61/123 204/403.06 |
| 5,215,631 | A | * | 6/1993 | Westfall .................. C30B 7/00 117/78 |
| 6,358,392 | B1 | * | 3/2002 | Yang ...................... B82Y 10/00 205/183 |
| 6,875,208 | B2 | * | 4/2005 | Santini, Jr. ........... A61K 9/0009 604/890.1 |
| 7,011,630 | B2 | * | 3/2006 | Desai ................ A61B 5/14532 204/403.01 |
| 9,320,832 | B2 | * | 4/2016 | Joseph .................... A61L 29/04 |
| 2002/0120186 | A1 | * | 8/2002 | Keimel ............. A61B 5/14865 600/365 |
| 2005/0143715 | A1 | * | 6/2005 | Cima .................. A61K 9/0009 604/890.1 |
| 2011/0003401 | A1 | * | 1/2011 | Oscarsson ............ B01J 19/0046 436/518 |

* cited by examiner

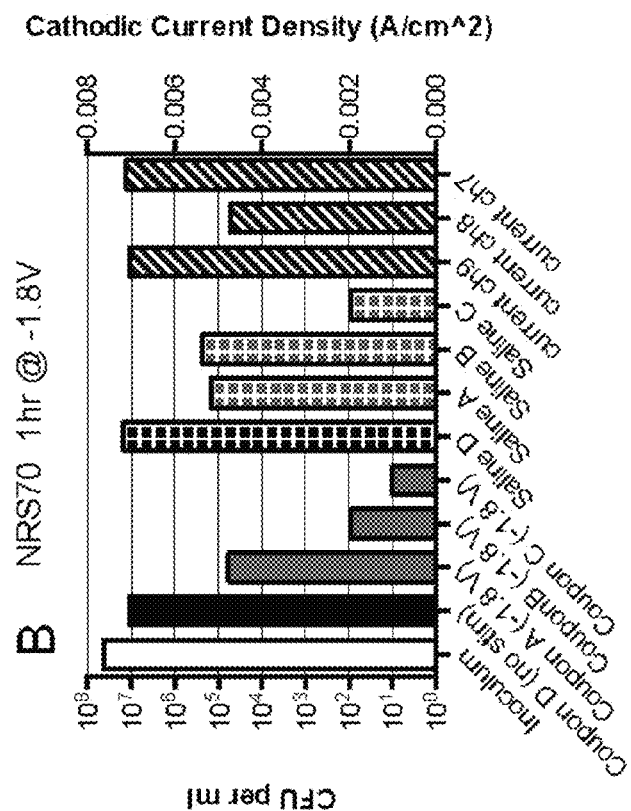
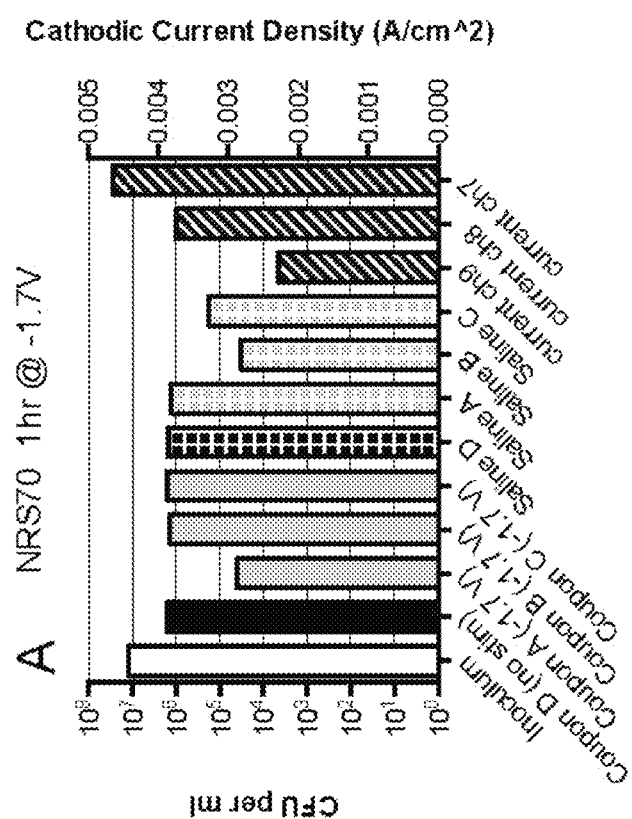
Fig. 11a-b

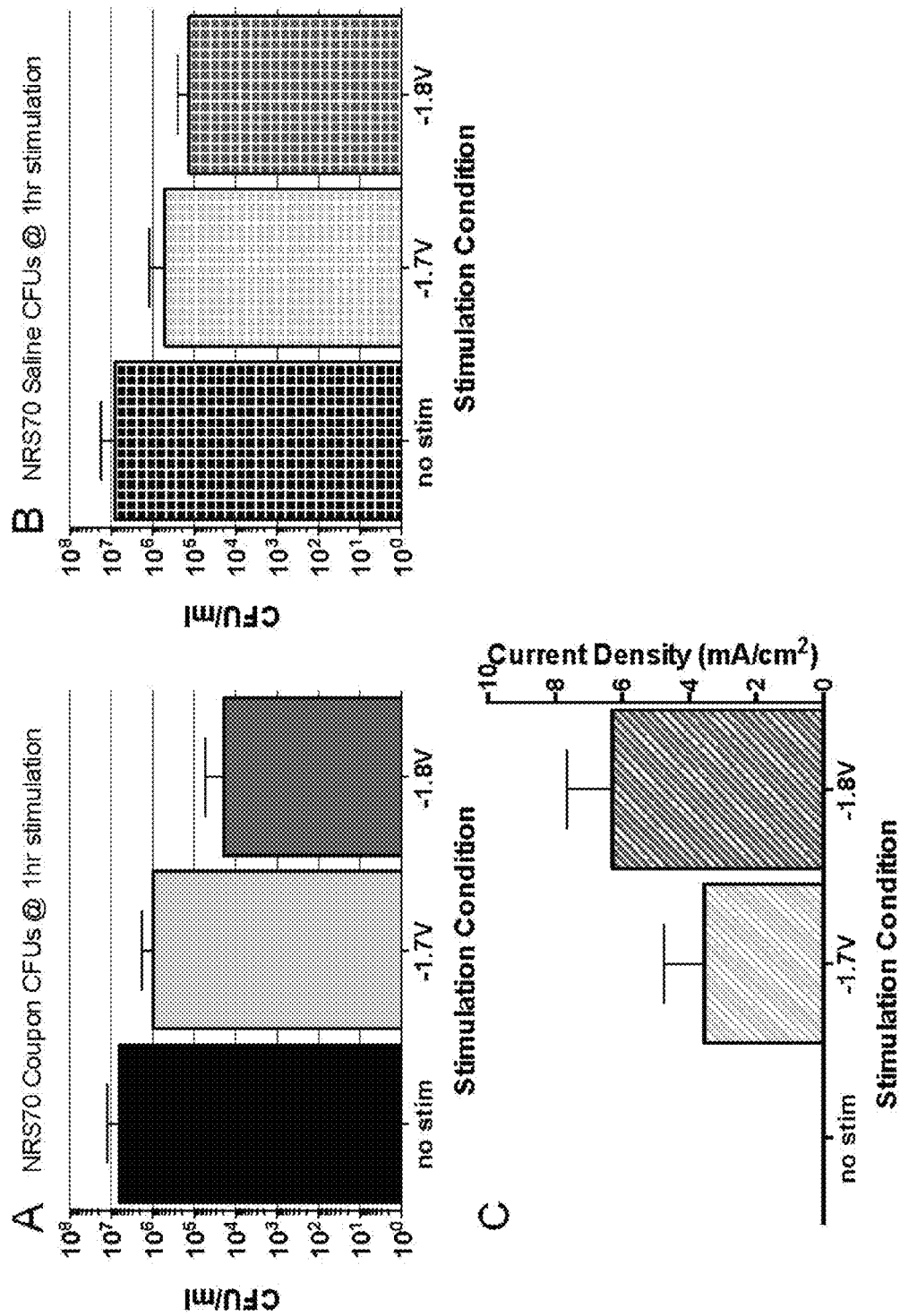
Fig. 12a-c

ELECTROCHEMICAL ERADICATION OF MICROBES ON SURFACES OF OBJECTS

CROSS-REFERENCE TO RELATED APPLICATIONS

This application is a continuation of U.S. application Ser. No. 14/395,640, filed Oct. 20, 2014, which is a National Phase of PCT/US2013/037637, filed Apr. 22, 2013, which claims priority to U.S. Provisional Application No. 61/636,349, filed on Apr. 20, 2012, and is a continuation-in-part of U.S. application Ser. No. 12/534,443, filed Aug. 3, 2009, the disclosures of each of which are incorporated herein by reference.

STATEMENT REGARDING FEDERALLY SPONSORED RESEARCH

This invention was made with government support under Contract W81XWH-10-1-0690 awarded by US Army Medical Research and Material Command. The government has certain rights in the invention.

FIELD OF THE INVENTION

The invention relates to devices and methods for the electrochemical eradication of microbes.

BACKGROUND OF THE INVENTION

Infection following repair or replacement implantations, such as orthopedic implants, is a devastating complication associated with increased patient morbidity, longer hospital stays, and increased costs to the health care system. In the case of total hip arthroplasty (THA) and total knee arthroplasty (TKA), the projected situation is particularly concerning. It has been projected that the number of primary THA and TKA procedures are expected to increase. The current annual incidence of periprosthetic joint infections (PJI) following TKA and THA is also projected to increase. Revision procedures due to infections are more expensive than revisions due to aseptic reasons. As such, the total economic burden of PJI has been projected to increase.

Persistent or recurrent infections have been reported in some of those patients that require revision surgery due to primary infection. One of the primary mechanisms by which bacteria resist decontamination and persist on implants is through the formation of biofilms. *Staphylococcus aureus* (*S. aureus*) and *Acinetobacter baumannii* (*A. baumannii*) are microbes of major concern. *S. aureus* is a gram-positive bacterium and is considered the main pathogen in infections around metallic implants. There is also a growing concern about the increased prevalence of methicillin-resistant *S. aureus* (MRSA) being isolated from infected orthopedic implants. *A. baumannii* is a gram-negative bacterium that is associated with implant biofilms and is being increasingly implicated in incidences of multidrug-resistance.

The bacteria in biofilms are significantly more resistant to antimicrobials as compared to planktonic bacteria. In fact, some biofilm infections are virtually impossible to cure with an antimicrobial (AM) alone and it is these persistent infections that necessitate the removal of orthopedic implants and debridement of the bone. Treatment options are limited for biofilm-associated implant infections. Typically infections are treated with broad-spectrum systemic antibiotics and/or revision surgery for possible lavage, debridement, implant removal, placement of local antibiotics, and perhaps implantation of a new device. However, with the current standard treatments, recurrence of orthopedic infections is frequently reported. In light of this, new approaches are needed for the prevention and/or eradication of device-related biofilm infections.

BRIEF SUMMARY OF THE INVENTION

In one embodiment, the invention may be described as a method of treating surfaces to make them resistant to the formation of microbe-associated biofilms. In one embodiment, the invention provides a method for reducing the number of or preventing the growth of microbes on the surface of an object. The microbes may be a part of a biofilm. The microbes may be bacterial or fungal microbes. The object is of such material that it can act as a working electrode. In another embodiment, the invention provides a method of reducing the number or preventing the growth of microbes in the tissues or fluids in proximity to the object.

In one embodiment, the method comprises the step of providing a counter electrode, a reference electrode, and a working electrode. The working electrode may comprise the entire object or a portion of the object. The method also comprises the step of passing electrical current through the working and counter electrodes. The current through the counter electrode is varied such that the electric potential of the working electrode is substantially constant relative to the electric potential of the reference electrode. The electric potential of the working electrode is such that the number of microbes on the object is reduced. In one such embodiment, the constant electric potential of the working electrode is selected from the range of about −0.5 to about −10.0 V with respect to the reference electrode.

In one embodiment, the object is implantable or implanted. The implantable or implanted object may have an oxide layer on at least part of the surface of the object. The oxide layer may spontaneously form on the surface when the object is exposed to, for example, air or biological material. In one embodiment, the implantable or implanted object is at least partially made from titanium or from a titanium alloy. In another example, the implantable or implanted object is at least partially made from stainless steel, cobalt, chromium, molybdenum, or any alloys or combinations thereof.

In another embodiment, the step of passing electrical current through the working and counter electrodes is performed using a potentiostatic device. The potentiostatic device may be a potentiostat, a computer-controlled instrument, or any other instrument capable of maintaining a substantially constant potential of a working electrode relative to a reference. In one embodiment, the reference electrode is at least partially made from silver or silver chloride. In another embodiment, the counter electrode is at least partially made from platinum or graphite.

In one embodiment, the method may further comprise the step of providing an antimicrobial agent to the material surrounding the object.

The invention may also be described as an apparatus for reducing or preventing microbes on a surface of an object. The object is of such material that it can act as a working electrode, and the object may be implanted or implantable. The apparatus comprises an electrical lead configured to be attached to the object such that, when attached, the object acts as the working electrode. The apparatus also comprises a counter electrode, a reference electrode, and a potentiostatic device, such as a potentiostat. The potentiostatic device is in electrical communication with the working electrode, the counter electrode, and the reference electrode. The potentiostatic device is configured to pass electrical current through the working and counter electrodes. The potentiostatic device is also configured to vary the current through the counter electrode such that the electric potential of the working electrode is substantially constant relative to an electric potential of the reference electrode. The electric potential of the counter electrode is such that the number of microbes or the growth of microbes on the surface of the object is reduced.

DESCRIPTION OF THE DRAWINGS

For a fuller understanding of the nature and objects of the invention, reference should be made to the following detailed description taken in conjunction with the accompanying drawings, in which:

FIGS. 11a-b are charts showing reductions of CFUs at −1.7V and −1.8V according to embodiments of the present invention;

FIGS. 12a-c are charts showing compiled and averaged data from FIGS. 11a-b;

DETAILED DESCRIPTION OF THE INVENTION

In one embodiment, the invention may be described as a method of treating surfaces to make the surfaces resistant to the formation of biofilms, such as biofilms comprising microbes. In one embodiment, the invention provides a method for reducing the number of microbes, reducing the growth of microbes, or preventing formation of biofilms comprising microbes on a surface of an object. The microbes may be a part of a biofilm or form a biofilm. The microbes may be any type of microbe that populate biofilms including, but not limited to, bacteria and fungi. The bacteria may be gram positive or gram negative. In one embodiment, the microbes may be in a planktonic form.

The object (or part of the object) is of such material that it can act as a working electrode, and the object may be an implanted or implantable object. For example, the object may be a portion of an implantable hip joint replacement. The implantable object may only be partially implanted. For example, the implantable object may be partially exposed outside of the body in which it is implanted, such as, for example, an external fixator pins used in fracture treatments. The implantable or implanted object may have an oxide layer on at least part of a surface of the object. For example, the implantable or implanted object is at least partially made from titanium. In another example, the implantable or implanted object is at least partially made from stainless steel, cobalt, chromium, molybdenum or any combination thereof.

Figure 2:
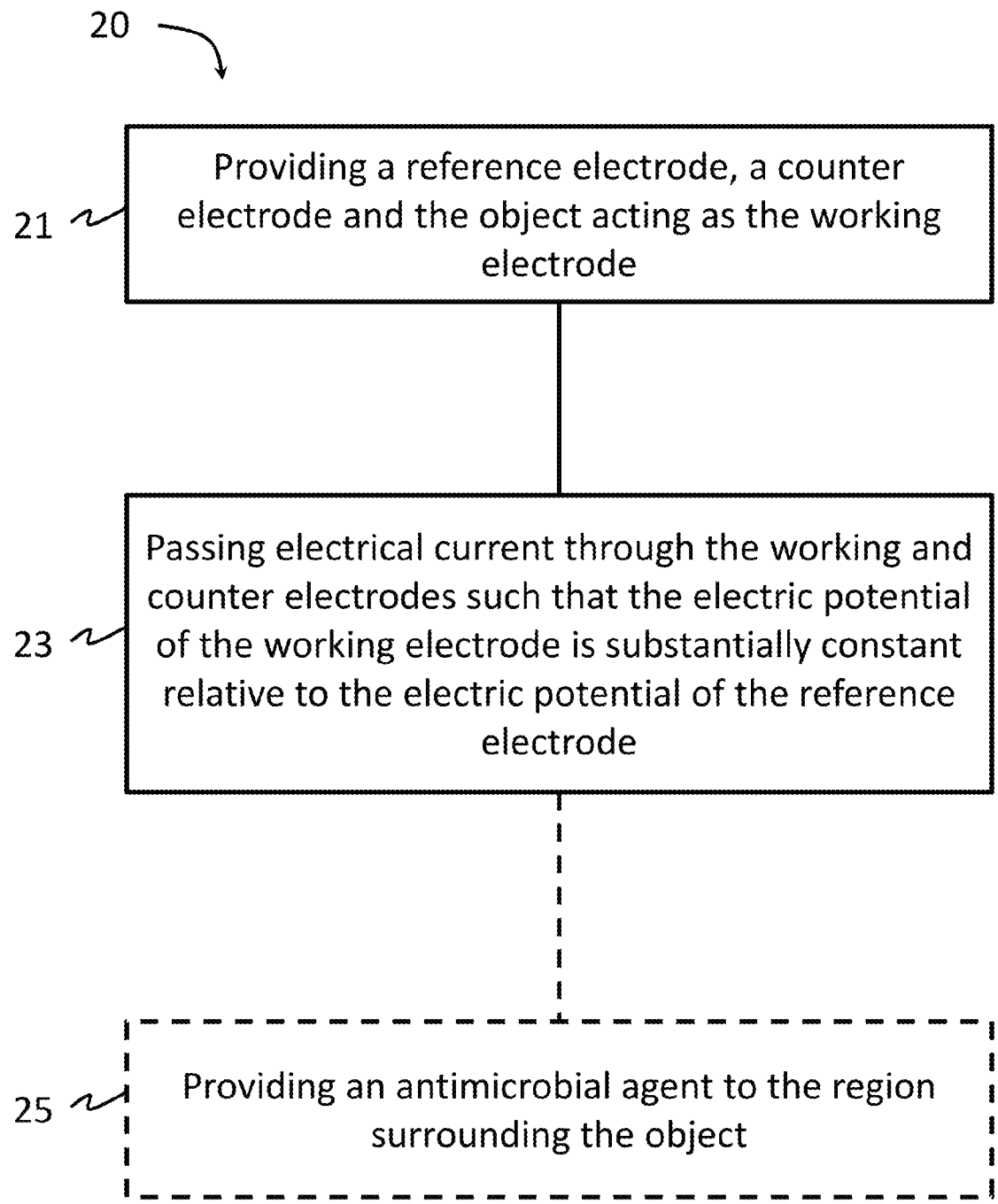
FIG. 2 is a flowchart illustrating a method of reducing microbes according to an embodiment of the present invention.
Figure 3:
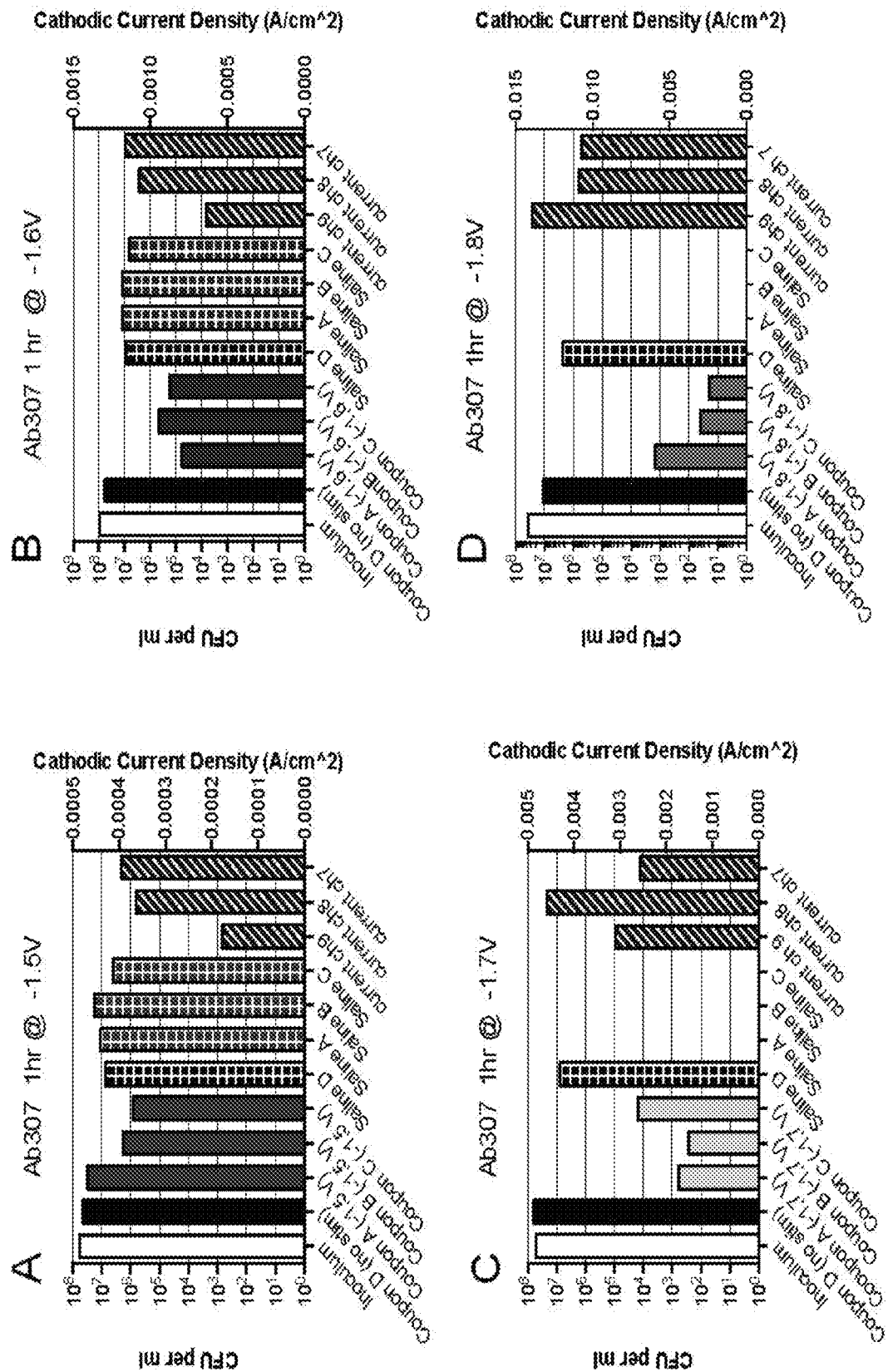
FIGS. 3a-d are charts illustrating constant cathodic voltage stimulation in eradicating preformed *Acinetobacter baumannii* (Ab307) biofilms using embodiments of the present invention.

FIG. 2 shows one embodiment of a method 20 of the present invention. The method 20 comprises the step of providing 21 a counter electrode, a reference electrode, and a working electrode. The working electrode comprises the object or a part of the object. The method also comprises the step of passing 23 electrical current through the working and counter electrodes. The current through the counter electrode is varied such that the electric potential of the working electrode is substantially constant relative to the electric potential of the reference electrode. In one embodiment, the electric potential of the working electrode does not vary more than 10%. In other embodiments, the electric potential of the working electrode does not vary more than 5%, 4%, 3%, 2%, or 1%. In another embodiment, the electric potential of the working electrode does not vary more than 10% after 1 minute of operation.

The electric potential of the counter electrode may be selected such that the number of microbes on the object is reduced. For example, a constant electric potential of the working electrode may be selected to be between −0.5 to about −10.0 V and all values therebetween to the tenth decimal place and all ranges therebetween with respect to the reference electrode. In one embodiment, the electric potential of the working electrode may be −0.5, −1.0, −1.5, −2.0, −2.5, −3.0, −3.5, −4.0 and −4.5 V vs. Ag/AgCl. The electrical current may be passed through the working and counter electrodes for various lengths of time.

In another embodiment, the step of passing 23 electrical current through the working and counter electrodes is performed using a potentiostatic device. The potentiostatic device may be a potentiostat, a computer-controlled instrument, or any instrument capable of maintaining a substantially constant potential in a working electrode relative to a reference. In one embodiment, the reference electrode is at least partially made from silver or silver chloride. In another embodiment, the counter electrode is at least partially made from platinum or graphite. The reference electrode may be placed in proximity to the working electrode or the counter electrode. For example, the reference electrode may be configured to wrap around (without contacting) the working or counter electrodes.

In one embodiment, the method may further comprise the step of providing 25 an antimicrobial agent to the material surrounding the object. For example, antibiotics may be injected or otherwise administered either systemically or locally into the region near the object. A synergistic effect may be achieved from this further step.

In another embodiment, the object may be medical equipment, an oil pipeline, a maple syrup pipeline, a water pipeline, a dairy pipeline, a food services utensil or other food services surface, or an HVAC component.

Figure 1:
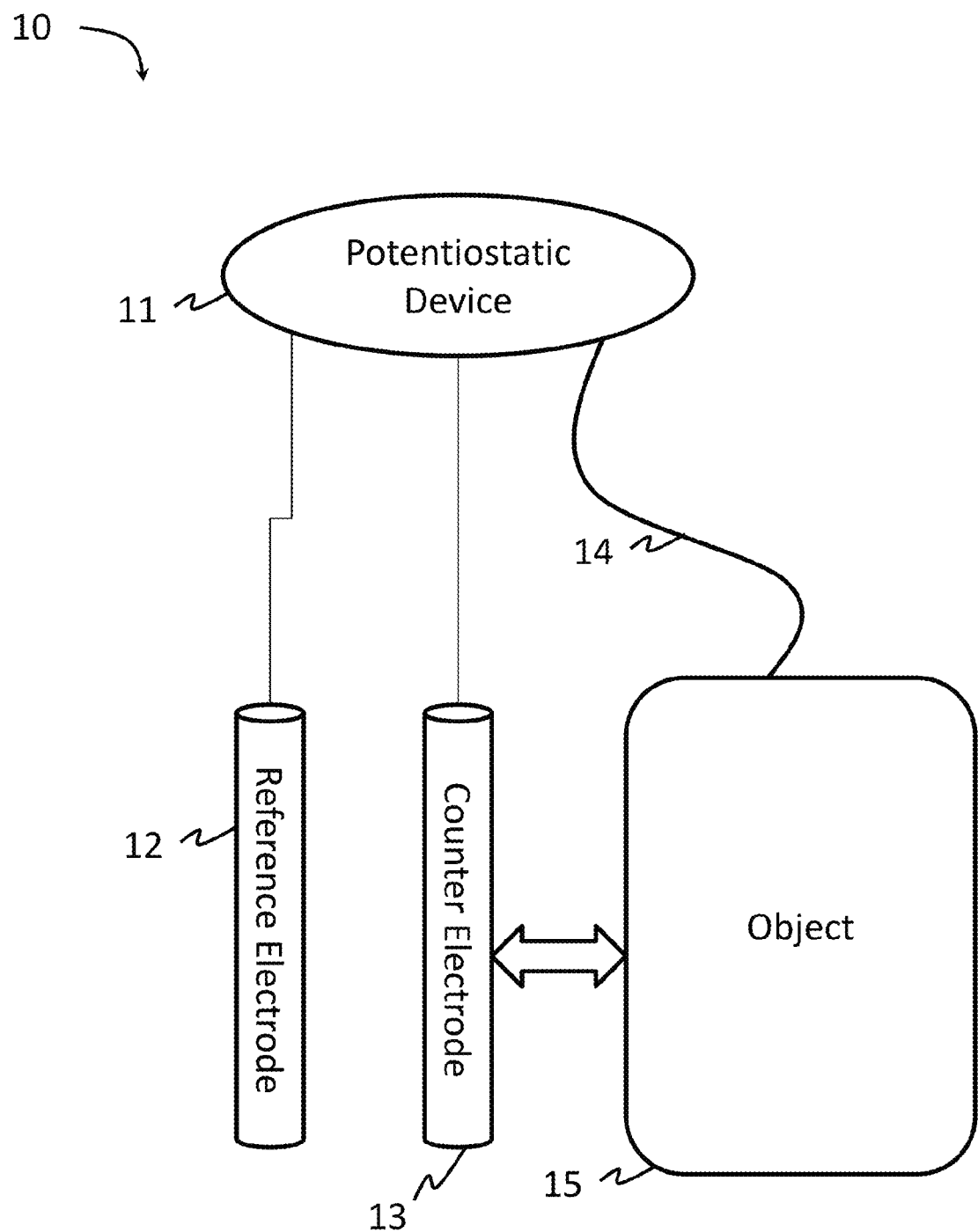
FIG. 1 is a schematic drawing of an apparatus in following with an embodiment of the present invention.

The invention may also be embodied as an apparatus 10 for reducing or preventing microbes on an object 15. One such embodiment is shown in FIG. 1. In some embodiments, the object 15 does not make up a part of the apparatus 10, but the apparatus 10 is configured to be attached to an object 15. The object 15 is of such material that it can act as a working electrode, and the object 15 may be implanted or implantable. The apparatus comprises a counter electrode 13, a reference electrode 12, a potentiostatic device 11, such as a potentiostat, and an electrical lead 14 configured to be attached to the object 15 such that, when attached, the object 15 acts as the working electrode. The potentiostatic device 11 is in electrical communication with the electrical lead 14, the counter electrode 13, and the reference electrode 12. The potentiostatic device 11 is configured to pass electrical current through the working electrode (when the electrical lead 14 is attached to the object 15) to the counter electrode 13. The potentiostatic device 11 is also configured to vary the current through the counter electrode 13 such that, when attached to the object 15, the electric potential of the working electrode is substantially constant relative to an electric potential of the reference electrode 12. The electric potential of the working electrode may be selectable such that the number of microbes on the object is reduced.

The invention may also be described as a method of inhibiting a microbial infection associated with an implantable or implanted object, wherein the object is of such material that it can act as a working electrode. The method comprises using the object as a working electrode, and further providing a potentiostatic device that is electrical communication with a reference electrode, a counter electrode, and the working electrode. An electric current is passed through the working and counter electrodes for a period of time using the potentiostatic device. The potentiostatic device maintains the working electrode at a substantially constant electric potential relative to the reference electrode, such that the microbial infection is inhibited.

The invention may also be described as a method of preventing the formation of a population of microbes such as associated with a biofilm, on the surface of an implantable or implanted object, wherein the object is of such material that it can act as a working electrode. The method comprises providing a reference electrode in electrical communication with a counter electrode, a working electrode and a potentiostatic device. The working electrode is the object or part of the object. An electrical current is passed through the working and counter electrodes, for a period of time using the potentiostatic device. The potentiostatic device maintains the working electrode at a substantially constant electric potential relative to the reference electrode, such that the microbial growth is prevented.

The invention may also be described as a method of removing or preventing the formation of a microbial biofilm on a surface, wherein the surface is of such material that it can act as a working electrode. The method comprises providing a reference electrode in electrical communication with a counter electrode, the working electrode, and a potentiostatic device. The working electrode comprises the surface. The method also comprises the step of passing electrical current through the working and counter electrodes, for a period of time using the potentiostatic device.

The potentiostatic device maintains the working electrode at a substantially constant electric potential relative to the reference electrode, such that the microbial biofilm is at least partially removed or prevented from forming.

The present invention may be described as a method of treating a microbial infection associated with an implantable or implanted object. A microbial infection is associated with an implanted or implantable object when one or more microbes are present on the object or on an oxide film formed on a surface of the object. The microbes may be part of a biofilm. The microbes may comprise gram negative or gram positive bacteria. The microbes may comprise fungi. The implantable or implanted object may be configured to act as a working electrode. At least part of the implantable or implanted object may be made from titanium. An electrode is an electrical conductor used to make contact with a nonmetallic part of a circuit (e.g., tissue). In one embodiment, the working electrode is a cathode of an electrochemical cell where reduction occurs.

In one embodiment, the method comprises the step of providing a potentiostatic device in electrical communication with a counter electrode, a reference electrode, and the working electrode (i.e., the implantable/implanted object). The potentiostatic device may be potentiostat or other device for controlling the voltage of the working electrode with respect to the reference electrode by forcing current to flow between the counter and working electrodes. In one embodiment, the counter electrode and the reference electrode are physically separated. The reference electrode may be made from silver or silver chloride. The counter electrode may be made from platinum, graphite, or a carbonized conductive silicone rubber or a gel-type transcutaneous stimulating electrode. The reference electrodes may be a pellet, wire, or disc-type electrode. The counter electrode may be a gel-type electrode, for example, a gel-type electrode that may be attached directly to the skin. A potentiostat is an electronic instrument that controls the voltage difference between a working electrode and a reference electrode. The potentiostat implements this control by injecting current into the system through a counter electrode.

The method further comprises the step of passing electrical current through the working and counter electrodes using the potentiostat. The electrical current may be passed for a period of time during which the working electrode maintains a substantially constant electric potential relative to the reference electrode, such that the number of microbes on the implantable/implanted object is reduced.

The concept of manipulating gram-negative (e.g. *S. aureus*) and gram-positive (e.g. *A. baumannii*) bacterial interactions with implants, such as titanium implants, by controlling the voltage-dependent electrochemical properties of the implant represents a new and unexplored approach to infection control for implants. This control can be exercised through a potentiostat or other device for controlling the voltage of the working electrode with respect to the reference electrode by forcing current to flow between the counter and working electrodes. It is important to emphasize that it is the voltage of the electrode that determines the specific electrochemical process that will occur at the electrode interface. The current simply indicates the rate of the dominant reaction.

Figure 8:
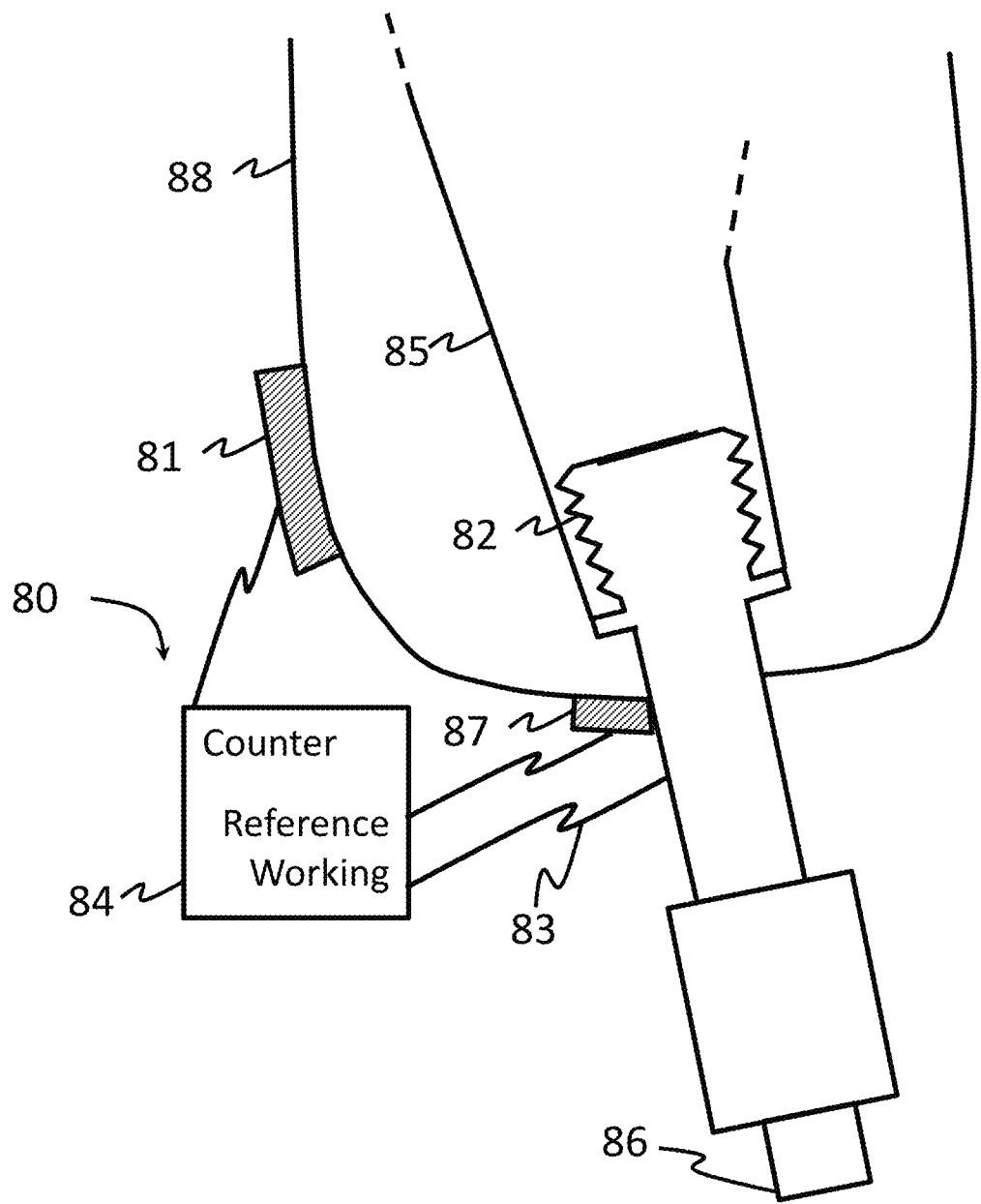
FIG. 8 is a diagram of one embodiment of an apparatus according to the present invention in use with an object.

This invention can be used for transcutaneous medical devices or medical devices that are contained completely internal when implanted. One such embodiment is shown in FIG. 8. The apparatus 80 comprises a potentiostatic electrical stimulation unit 84. In the case of osseointegrated prosthetic limbs, or dental implants, or external fixator pins the transcutaneous abutment 86 or pin may directly be connected to the potentiostatic electrical stimulation unit 84 so that the implant 82 (including abutment 86) functions as the working electrode. Skin surface electrodes 81 may be carbonized conductive silicone rubber electrodes or gel-type stimulating electrodes would be utilized as the counter electrode and would be connected using wire 83 to the potentiostatic electrical stimulation unit 84. A pellet, wire, or disc-type Ag/AgCl reference electrode 87 would also be placed on the skin 88 in close proximity to the transcutaneous site and would be connected to the potentiostatic electrical stimulation unit 84. The implant 82 (including abutment 86) may be mounted to bone 85.

Figure 9:
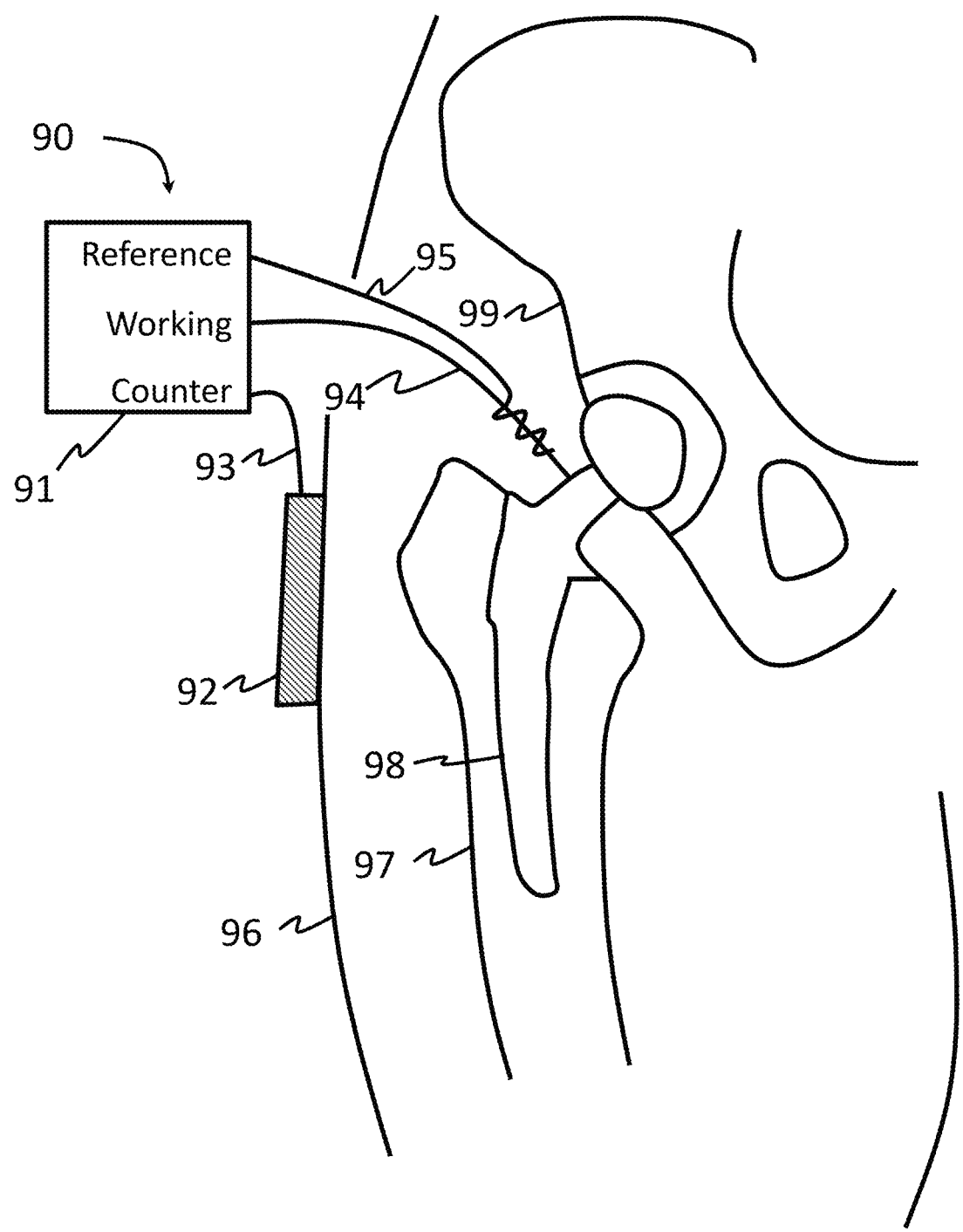
FIG. 9 is a diagram of another embodiment of an apparatus according to the present invention in use with a hip-replacement implant.

Alternatively, completely internal implants may be treated in a minimally invasive manner by inserting an electrically conductive material (sterile wire or sterile needle) to contact the implant and connect it, as a working electrode, to an external potentiostatic electrical stimulation unit. One such device 90 is shown in FIG. 9. Insertion of the needle through skin 96 may be performed under local or systemic anesthesia. Surgery may also be employed to connect the implant 98 to a voltage source, such as a battery, which contains a mechanism for controlling the voltage source. Surgical techniques can also be employed to attach to the implant an electrical attachment, such as a sterile wire 94, connected to the implant and implanted such that at any time post-implantation, the electrical attachment can be accessed and connected to a voltage source. Skin surface electrodes 92, such as carbonized conductive silicone rubber electrodes or gel-type stimulating electrodes would be utilized as the counter electrode and would be connected using a lead 93 to the potentiostatic electrical stimulation unit 91. In one embodiment, a counter electrode 95 may be wrapped around the sterile wire 94. In another embodiment, a pellet, wire, or disc-type Ag/AgCl reference electrode would also be placed on the skin in close proximity to the transcutaneous site and would be connected to the potentiostatic electrical stimulation unit. Alternatively, the reference electrode and counter electrode may also be inserted internally and make electrical contact with the external potentiostatic electrical stimulation unit. The implant 98 may be osseointegrated into bones 97 and 98.

Figure 10:
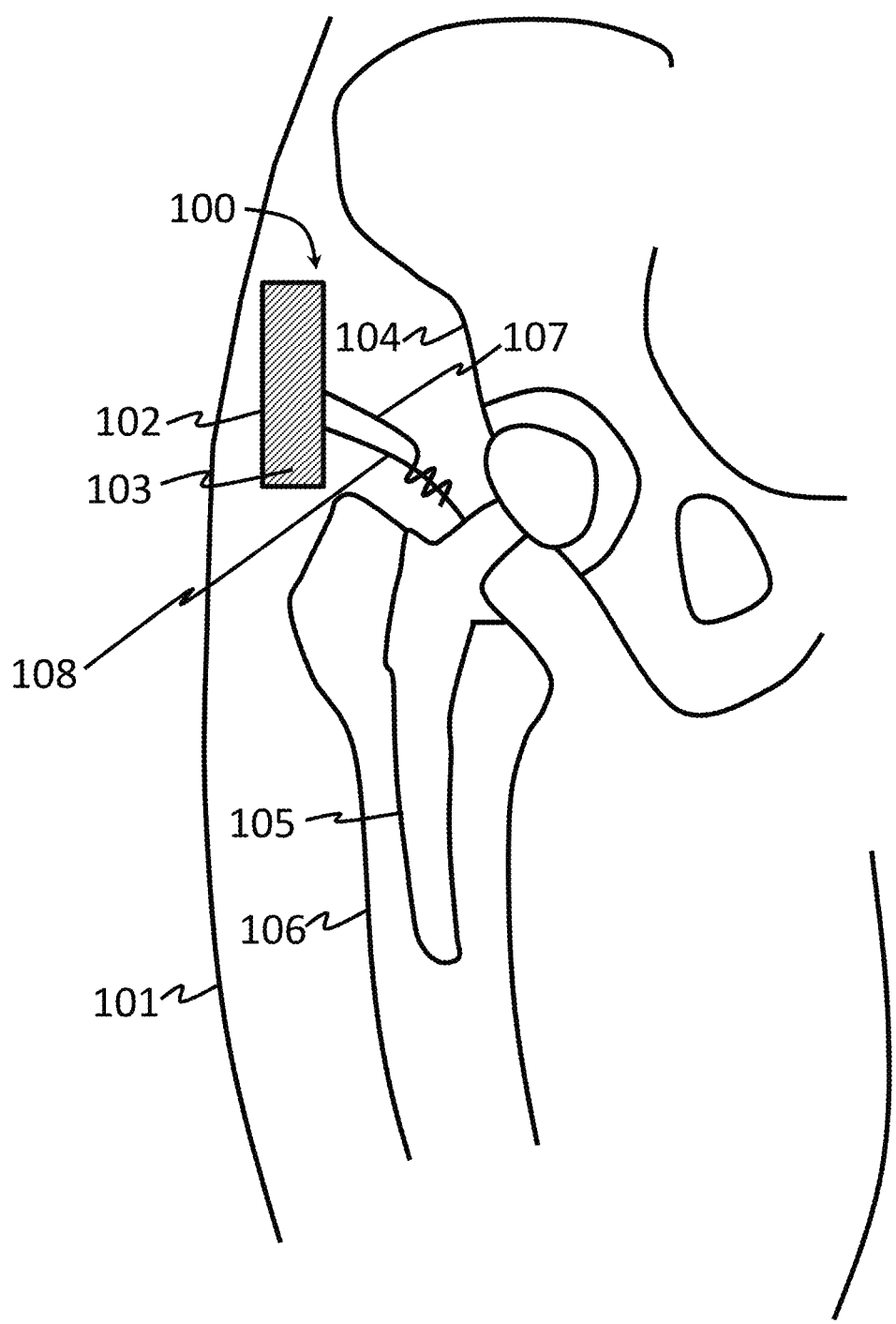
FIG. 10 is a diagram of another embodiment of an apparatus according to the present invention in use with a hip-replacement implant.

In another embodiment, as shown in FIG. 10, the completely internal implant 105 (here, internal to the skin 101) may treated by connecting it as the working electrode to a potentiostatic electrical stimulation unit 103 that is itself implanted internally in the body (here within bones 104 and 106). The connection may be performed through the use of an electrical lead 108. The voltage source of these potentiostatic electrical stimulation units 103 may be a battery or may be a wireless, inductively charged power source. The implant 105 would be electrically connected as the working electrode to the potentiostatic electrical stimulation unit 103. A counter electrode 107, composed in part of platinum, and reference electrode 102, composed in part of silver or silver chloride will also be implanted and connected to the potentiostatic electrical stimulation unit 103. The reference electrode 102 may be part of the potentiostatic electrical stimulation unit 103, such as the housing. These implants may contain advanced wireless telemetry units that will enable the real-time control and monitoring of the implant electrochemical properties and stimulation parameters.

In another embodiment, completely internal implants may be manufactured with a potentiostatic electrical stimulation and control unit embedded with in the design of the implant. The voltage source of these potentiostatic electrical stimulation units may be a battery or may be a wireless, inductively charged power source. The implant would be electrically connected as the working electrode to the potentiostatic electrical stimulation unit. A counter electrode, composed in part of platinum, and reference electrode, composed in part of silver or silver chloride will also be implanted and connected to the potentiostatic electrical stimulation unit. These new implants may contain advanced wireless telemetry units that will enable the real-time control and monitoring of the implant electrochemical properties and stimulation parameters.

In one embodiment, the implant may have an external fixation pin such that a potentiostatic device may be attached. In another embodiment, a loop of conductive material may be cinched around an implant in order to maintain electrical conductivity between the potentiostatic device and the implant.

Our experiments have shown that using these disclosed systems and methods to control the cathodic potential of titanium can reliably and quickly treat implant infections by eradicating biofilms comprising *A. baumannii* without requiring AMs. AMs may, however, be incorporated within the scope of the invention. Furthermore, cathodic stimulation has been shown to enhance bone formation. Therefore, the same system can, after treating the infection, be switched into a voltage range that promotes bone healing.

Titanium's relatively high corrosion resistance is an important factor in its biocompatibility. The standard electrode potential for titanium is −1.6 V (vs. normal hydrogen electrode), which implies there is a large thermodynamic driving force for titanium to oxidize. However, when exposed to air or solution titanium spontaneously passivates with a surface oxide layer, which acts as a kinetic barrier to prevent corrosion of the titanium. Therefore, despite being an active metal, titanium exhibits the high corrosion resistance due to the presence of the oxide film and not due to the properties of bulk titanium. This oxide film is truly the "surface" of titanium that is presented to and interacts with the biological environment.

Most metals used for orthopedic applications (stainless steel, cobalt chromium molybdenum alloys, Ti-alloys such as Ti6Al4V) have oxide films that are governed by a high-field mechanism, and so this voltage-controlled decontamination method can be used for those materials as well. Other alloys of these metals are also within the scope of the invention.

The voltage of titanium (or other working electrode) is a factor because it dictates the formation, growth, modification, and electrochemical impedance of the oxide film. As the voltage increases in the positive direction the oxide film will grow (anodization) and as the voltage increases in the negative direction the oxide film will thin as a result of chemical composition changes (reductive dissolution). Titanium oxide film displays n-type semiconductor behavior that is also dependent upon the voltage of the titanium. For example, biasing titanium to potentials below the oxide's flat-band potential (~350 mV) can induce a negative surface excess charge within the semiconducting oxide due to a surface accumulation of electrons. This can enhance the electronic current conduction at the interface and it can also alter the space charge layer of the oxide. We have also reported recently that the electrochemical impedance of the titanium-oxide-solution interface is strongly dependent on the voltage. The outcomes showed that in comparison to the open circuit condition or the anodic voltage range, the cathodic voltage range (−1000 mV to −600 mV vs. Ag/AgCl) had an interfacial resistance (measure of Faradic processes) that was orders of magnitude lower and produced a large cathodic current density. In addition the interfacial capacitance (measure of non-Faradaic processes) was significantly higher in this cathodic range. We also recently showed that pre-osteoblasts have decreased in vitro biocompatibility with titanium when titanium was polarized to the cathodic voltages (−1000 mV and −600 mV vs. Ag/AgCl). The cellular results were correlated to the increased Faradaic and non-Faradaic processes at these potentials. Therefore, it can be stated that precise control of titanium's voltage is crucial to understanding its electrochemical properties and subsequent interactions with a biological system, such as a bacterial biofilm.

Based on the above findings with respect to pre-osteoblasts, we initially applied −0.5 to −1 V vs. Ag/AgCl to titanium implants. However, we surprisingly found better results using −1.5 to −1.8 V vs. Ag/AgCl.

In various embodiments, the voltage applied may be around −1.5, −1.6, −1.7, or −1.8 V vs. Ag/AgCl. Any voltage between −0.5 to −10.0 V vs. Ag/AgCl and any voltage there between to the tenth of decimal place can be applied to the working titanium electrode. In various embodiments, the voltage may be −0.5 to −5.0 V vs. Ag/AgCl, such as −0.5, −1.5, −2.0, −2.5, −3.0, −3.5, −4.0 and −4.5 V vs. Ag/AgCl. Any cathodic current density from 8 $\mu A/cm^2$ to 10 $mA/cm^2$ may be used to maintain the potential of the titanium working electrode vs. Ag/AgCl system, preferably from 80 $\mu A/cm^2$ to 10 $mA/cm^2$. In some embodiments, the voltage range may be between −0.5 to −3.0 V vs. Ag/AgCl or −0.5 to −10.0 V vs. Ag/AgCl depending on the length of application to the working titanium electrode. In a situation where a more negative voltage is applied, the use of pain suppressants, sedatives, or anesthetics may be utilized for the procedure.

The treatment of the surfaces may be carried out for relatively short treatment periods of time, such as from a minute to an hour. However, the duration may be chosen based on, for example, the extent of the microbial infestation. Thus, treatment time may range from 1 minute to 1 year and any interval of time in between. For example, a high voltage may be applied for a short period of time (1 minute to 1 hour), or a low voltage may be applied for longer periods of time (such as up to 1 year or even longer as needed). In one embodiment, the detection of infection in an individual may dictate the length of time needed for the application of voltage. For example, routine methods (such as clinically used methods for detection of systemic or localized infection), may indicate to a clinician the need for continued treatment by the method of the present invention. Conversely, a diagnosis of absence or amelioration of the systemic or localized infection may indicate to a clinician that the application of voltage may be reduced or stopped. If needed, the treatment may be done at a low intensity during periods of high risk due to infection. A second range of voltages may be applied to the same object for bone healing or bone cell generation.

In one embodiment, a method of the present invention is used in combination with other antimicrobial treatments. For example, it can be used in combination with the administration of antibiotics. The antibiotics may be delivered systemically or may be delivered locally. The antibiotics may be broad spectrum antibiotics or may be particularly effective against certain bacteria. In one embodiment, the antibiotic is effective against *S. aureus* and/or *A. baumannii*. The antimicrobial treatment can be carried out before, during, or after the application of voltage as described herein.

In two-electrode constant current systems, stimulation is achieved by adjusting a potential difference between the pair of electrodes, regardless of their individual absolute potentials relative to a stable reference electrode, to maintain the flow of constant current. Therefore, precise control of the electrode voltage is not provided, and, in fact, it has shown that the voltage of the anode and cathode in constant current systems can vary widely with respect to stable reference electrode. This further shows that different electrochemical processes can take place at the electrode surface as the voltage of the electrodes drift, which may promote different or irregular consequences within the biological environment.

The importance of controlling the voltage has not previously been recognized in the field. We treated implant infections using our three-electrode system with a potentiostat or other device for controlling the voltage of the working electrode with respect to the reference electrode by forcing current to flow between the counter and working electrodes. Our system delivers constant voltage stimulation to an implant, such as a titanium orthopedic implant, that is connected as the working electrode. To our knowledge, there are no reports of voltage-controlled titanium in a three-electrode configuration influencing biofilm formation or eradication.

The systems and methods disclosed here allow for precise voltage-control of the working electrode, such as titanium, and consequently its electrochemical properties. The system comprises (and the method utilizes) a working electrode, a counter electrode, a reference electrode and a potentiostat or other device for controlling the voltage of the working electrode with respect to the reference electrode by forcing current to flow between the counter and working electrodes. It is the surface potential of the working electrode that we are controlling. However, in order to control or measure the working electrode surface potential another electrode (the reference electrode) must be introduced. This second electrode also has its own surface potential. Neither the working electrode surface potential nor the second electrode surface potential can be determined independently. The potential difference measured between these two electrodes is the summation of the two surface potentials. Therefore, if one of the surface potentials is constant, reliable measurements can be made of how the second potential varies. A reference electrode (e.g., Ag/AgCl) is designed to have a very stable potential and is therefore utilized as the second electrode. In this regard the voltage of the working electrode is measured or controlled with respect to the reference electrode (e.g., Ag/AgCl). In order to control the voltage of the working electrode, electrons must be able to be moved towards or away from the working electrode. However, this current cannot pass through the reference electrode because this may alter the reference electrode surface potential. Therefore, a third electrode, the counter electrode, is utilized to conduct current and complete the circuit. In order to not limit electrochemical processes at the working electrode, the counter electrode should be of greater surface area than the working electrode and be composed of a material that easily conducts current. Platinum and graphite are commonly used materials for counter electrodes. This separation of the current conducting electrode (counter) and the reference potential electrode (reference) is critical to applications where accurately controlling the voltage of the working electrode is important. In some embodiments, the electrodes and potentiostatic device may be shielded in order to prevent interference with electrically sensitive tissue.

Another component is a potentiostat or other instrument that controls the voltage of working electrode with respect to the reference electrode by forcing current to flow between the counter and working electrode. Potentiostats are well known in the art. These can be made or commercially obtained. There are a variety of bench-top potentiostats that are commercially available. Applying a constant voltage instead of a constant current may help to reduce the amount of time needed for treatment. Furthermore, in a constant-current system, the voltage of the working electrode may drift into ranges that trigger muscular firing or cause discomfort or pain to a user. The constant voltage systems and methods as described herein may be advantageous because the electrochemical processes can be more accurately and immediately controlled than in a constant-current system.

This voltage-controlled method of biofilm eradication can be broadly applied. This method can also be used for inhibiting or preventing the growth of microbes in planktonic form. For instance, it can be used in the following titanium implanted medical device categories: dental implants; osseointegrate prosthetic limbs; fracture fixation plates, screws, and rods; external fixation pins; hip, knee, ankle, shoulder, elbow, wrist, and intervertebral disc replacements; and spine fixation hardware. Other potential applications of biofilm eradication include: durable medical equipment sterilization; oil industry/pipelines; maple syrup pipelines; water sanitation pipelines; dairy production pipelines; food services sterilization of surfaces and utensils; and HVAC components sterilization.

EXAMPLE 1

Test coupons made from commercially pure titanium (cpTi, Ti Industries), were sequentially wet sanded through 600 grit, ultrasonically cleaned in deionized water, and sterilized under UV light for 30 mins. The test coupons were then incubated (37 C at 100 rpm) in freshly inoculated bacterial cultures (containing ~$10^4$ colony forming units (CFU) per ml in Mueller-Hinton media) for biofilm formation. After incubation for 1 hr or 18 hrs, biofilms of $10^4$ CFUs or $10^7$ CFUs, respectively, formed on the cpTi coupons.

Clinical isolates were utilized of both Gram-negative *Acinetobacter baumannii* and Gram-positive methicillin-resistant *Staphylococcus aureus*. *A. baumannii* strain 307-0294 (Ab307) was used. These isolates have a complete lipopolysaccharide, possess a capsule, form a biofilm, and are virulent in rat soft tissue infection models. The *S. aureus* strain is NRS70. This biofilm-forming MRSA strain is a respiratory isolate, sequence type 5, clonal complex 5. The genomes of both strains have been sequenced and are publically available.

Following incubation for biofilm formation, the cpTi was extracted from the bacterial culture, rinsed with sterile phosphate-buffered saline (PBS) and introduced into a ballistics gel chamber well designed to simulate soft tissue surrounding an implant. The chamber utilizes a three-electrode configuration to control the voltage of the cpTi (working electrode). A graphite counter electrode and an Ag/AgCl reference electrode were also placed in separate wells within the ballistics gel chamber. All voltages were measured with respect to the reference electrode (i.e., vs. Ag/AgCl). Approximately 1 mL of sterile saline were added to each electrode site to ensure a conductive pathway over the entire electrode surface. Electrical connections were made to a potentiostat (ref600, Gamry Instruments) to control the voltage of the cpTi. Cathodic voltage-controlled electrical stimulation was delivered to the cpTi for variable amounts of time. A 1 hr stimulation time was utilized in most experiments, but is variable. Following stimulation, the cpTi coupons were extracted from the ballistics gel chamber, washed with PBS, and surviving bacteria were released by sonication and dilution plated to enumerate biofilm CFUs. The saline surrounding the cpTi in the chamber was also sampled and dilution plated to assess for planktonic CFUs. The synergistic role of electrical stimulation coupled with antibiotic therapy can also be evaluated in this chamber by adding various concentrations of drugs to the sterile saline that surrounds the cpTi during the stimulation.

EXAMPLE 2

The next sets of experiments were conducted to explore the role of constant cathodic voltage stimulation in eradicating preformed Ab307 biofilms (18 hr incubation, ~$10^7$CFUs) on cpTi. We conducted a series of experiments to evaluate the application of constant cathodic voltage stimulation at −1.5V, −1.6V, −1.7V, and −1.8V for 1 hr. Post-stimulation CFUs were enumerated from both the coupons (biofilm bacteria) and the surrounding saline (planktonic bacteria). Samples that received no stimulation were assessed as controls. The outcomes of these individual experiments are presented in FIGS. 3a-d.

FIGS. 3a-d show plots of the experimental outcomes for constant cathodic potentials of −1.5V(a), −1.6V(b), −1.7V (c), and −1.8V(d) applied for 1 hours to cpTi samples with preformed biofilms of Gram-negative *A. baumannii* (Ab307). Each plot contains the biofilm CFUs enumerated from coupon of no stimulation controls (solid black bar) and experimental stimulations (−1.5V, −1.6V, −1.7 V, and −1.8V). The inoculum (white) indicates the initial pre-stimulated CFUs contained on each cpTi coupon. Also present in each plot are the planktonic CFUs (bars with grid) enumerated from the saline surrounding the no stimulation controls and the experimental stimulation conditions (−1.5V, −1.6V, −1.7 V, and −1.8V). The average cathodic current density associated with each channel during the applied voltages is also shown in all plots as bars with white slashes. The CFU axis is on the left while the current density axis is on the right.

Figure 4:
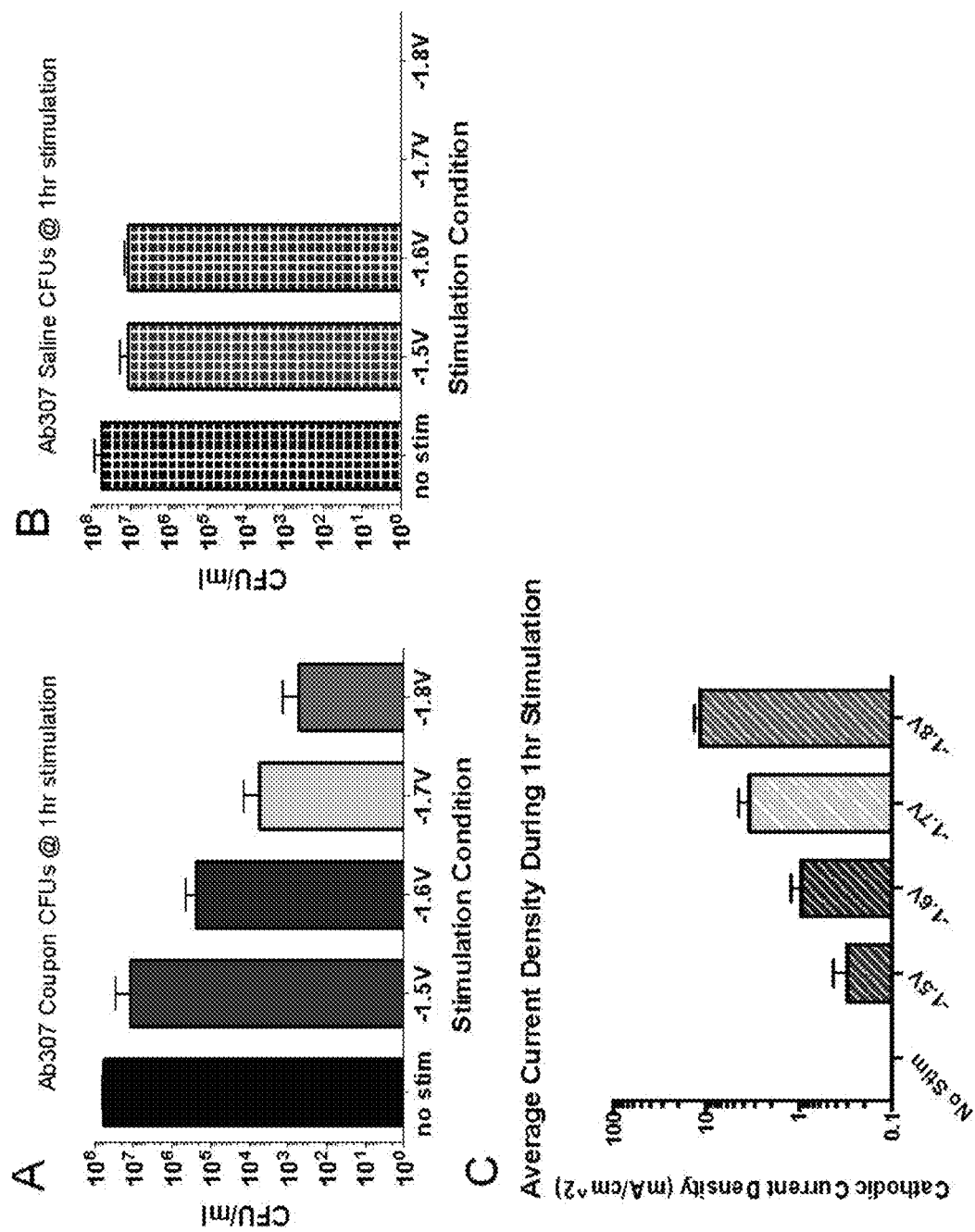
FIGS. 4a-c are charts showing average results for coupon Colony Forming Units (CFUs), saline CFUs, and variable current densities using embodiments of the present invention.

The individual data sets presented in FIGS. 3a-d were further analyzed and the average results for coupon CFUs, saline CFUs, and current densities at each experimental condition are shown in FIGS. 4a-c. Reductions in CFUs from the coupons were reported at increasing cathodic voltage. Specifically, stimulation at −1.6V, −1.7V, and −1.8V showed statistically significant reductions as compared to the unstimulated controls. The coupon CFUs at −1.7V and −1.8V were similar to each other, but significantly smaller than the CFUs at −1.5V and −1.6V, which were also similar to each other. No CFUs were obtained from the chamber saline at −1.8V or −1.7V, while CFUs obtained from chamber saline following exposure to −1.6V and −1.5V were comparable to the unstimulated controls. The current density at −1.5V and −1.6V were each different from all other groups. The current densities were largest at −1.7V and −1.8V, which were not different from each other. The main conclusion from these experiments is that cathodic polarization of cpTi induces significant bactericidal activity versus *A. baumannii* in biofilm (reduced coupon CFUs) and in planktonic (reduced saline CFUs) form in a voltage dependent manner.

FIGS. 4a-c: Plots of the average CFUs enumerated from the coupons (4a) and saline (4b) for each 1 hour stimulation condition. The average cathodic current density for each 1 hour stimulation condition is also shown in (4c).

EXAMPLE 3

Figure 5:
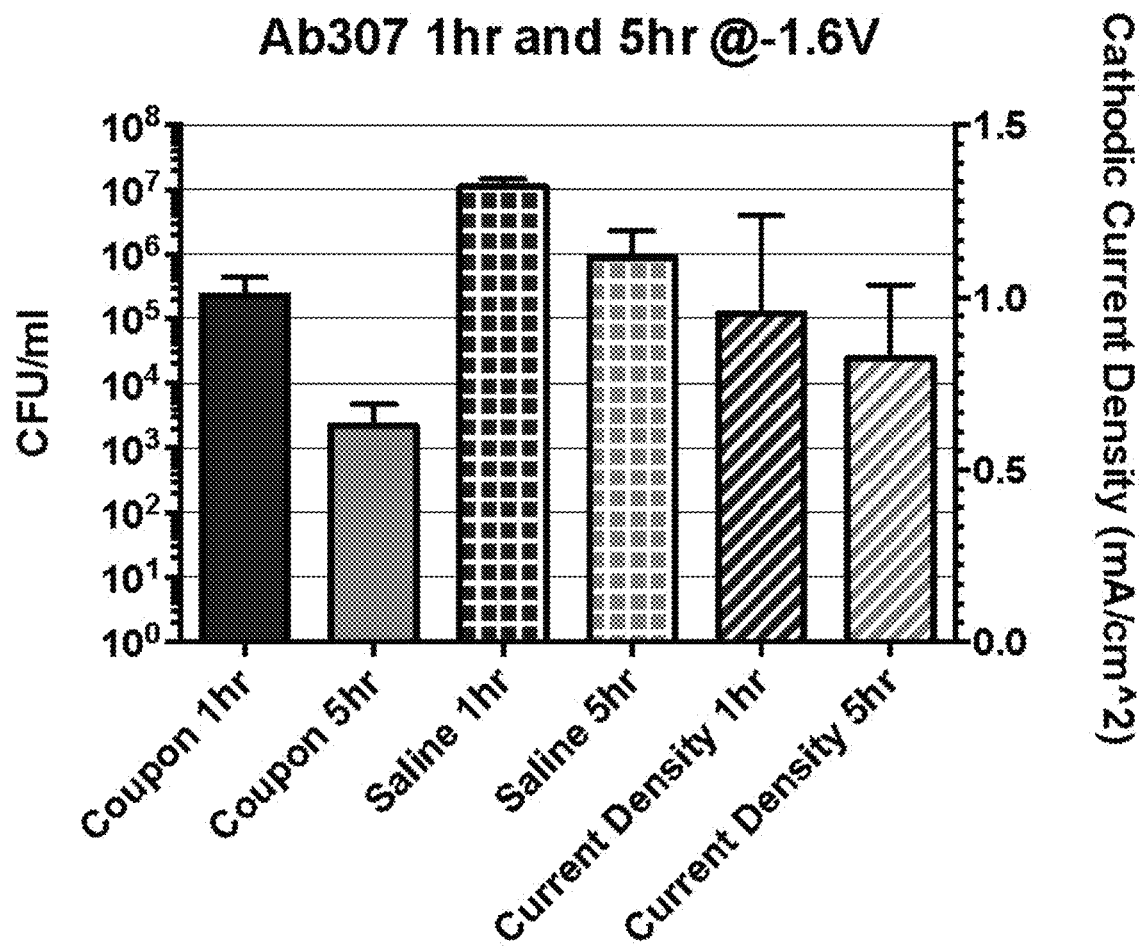
FIG. 5 is a chart showing reduction of CFUs with increased stimulation time according to embodiments of the present invention.

Based upon the data shown in FIGS. 4a-c we decided to focus on the effectiveness of the −1.6V stimulation because it showed significant reductions in biofilm CFUs and its current density hovered around −1 mA/cm$^2$ which is on the threshold of perception for stimulation. We subsequently performed a series of experiments in which −1.6V stimulation was delivered to cpTi samples with preformed Ab307 biofilms (18 hr incubation, ~10$^7$CFUs) for either 1 hr or 5 hrs. The averaged outcomes (FIG. 5) showed that the increased 5 hr stimulation reduces the CFUs enumerated from the coupon and the saline as compared to the 1 hr stimulation time, but that the current density remains same. Therefore, increasing stimulation time is an effective means to further reduce CFUs of both biofilm and planktonic Ab307. FIG. 5 shows a plot of the average CFUs enumerated from the cpTi coupons and the surrounding saline following −1.6V stimulation for 1 hour or 5 hours. Also shown is the average cathodic current density through the 1 hour or 5 hour stimulation period. The CFU axis is on the left while the current density axis is on the right.

EXAMPLE 4

Figure 6:
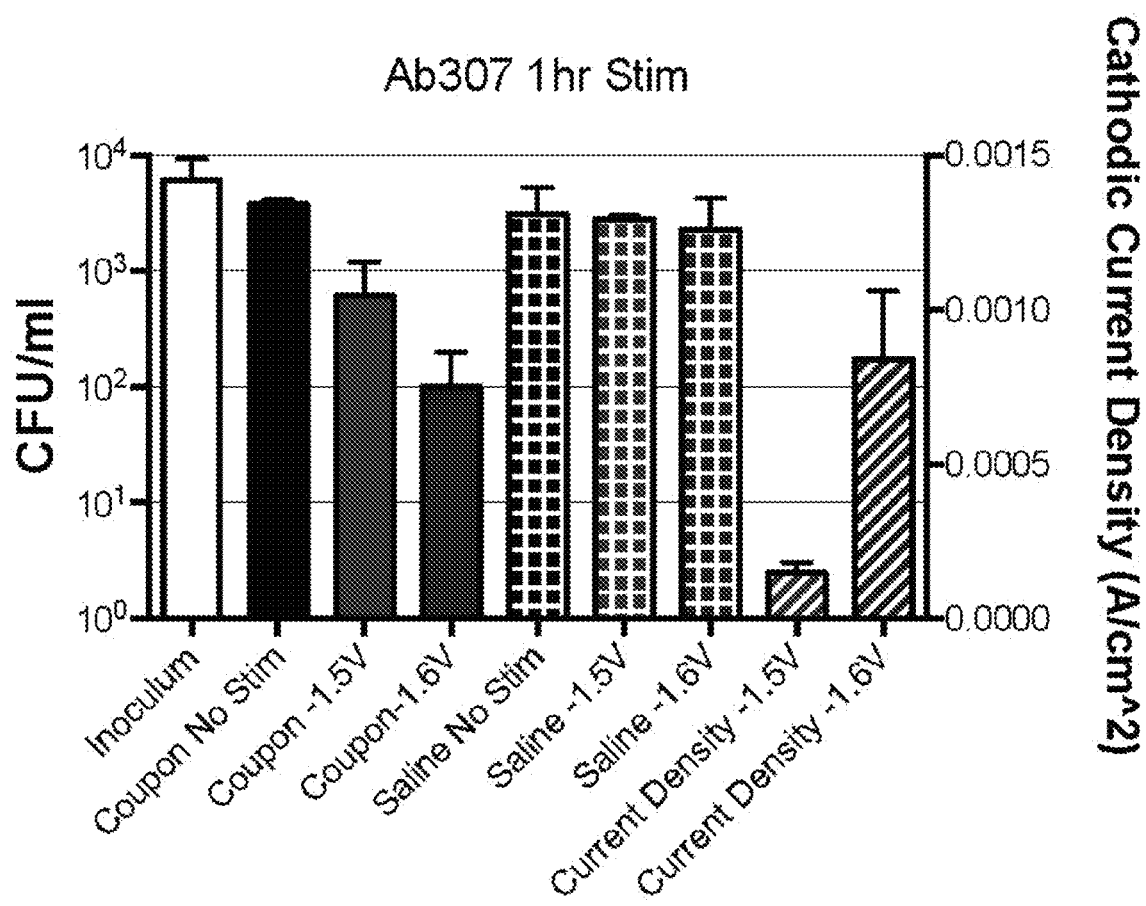
FIG. 6 is a chart showing reductions of CFUs at −1.5V and −1.6V according to embodiments of the present invention.

While the increased stimulation time decreased the CFUs relative to the shorter stimulation there were still 10$^3$-10$^4$ biofilm CFUs and ~10$^6$ planktonic CFUs present post-stimulation. We wanted to explore how we could further reduce or eradicate these remaining CFUs. To do this we initiated a new series of experiments with preformed biofilms that contained ~10$^4$ CFUs of Ab307. These lower CFU biofilms were prepared by incubating the cpTi coupon with the bacterial cultures for 1 hr as opposed to 18 hrs when preparing 10$^7$ CFU biofilms. The averaged outcomes of experiments conducted with 1 hr of stimulation at −1.5V and −1.6V are shown on FIG. 6. The mean values of the biofilm CFUs decrease as a function of cathodic voltage while the mean values of the planktonic CFUs are similar regardless of stimulation. However, even starting with the lower CFU biofilm, biofilm and planktonic bacteria still remain following stimulations. FIG. 6 shows a plot of the average CFUs enumerated from the coupon and the saline following 1 hr stimulation of cpTi that has a preformed Ab307 biofilm of ~10$^4$ CFUs. The CFU axis is on the left while the current density axis is on the right.

EXAMPLE 5

Figure 7:
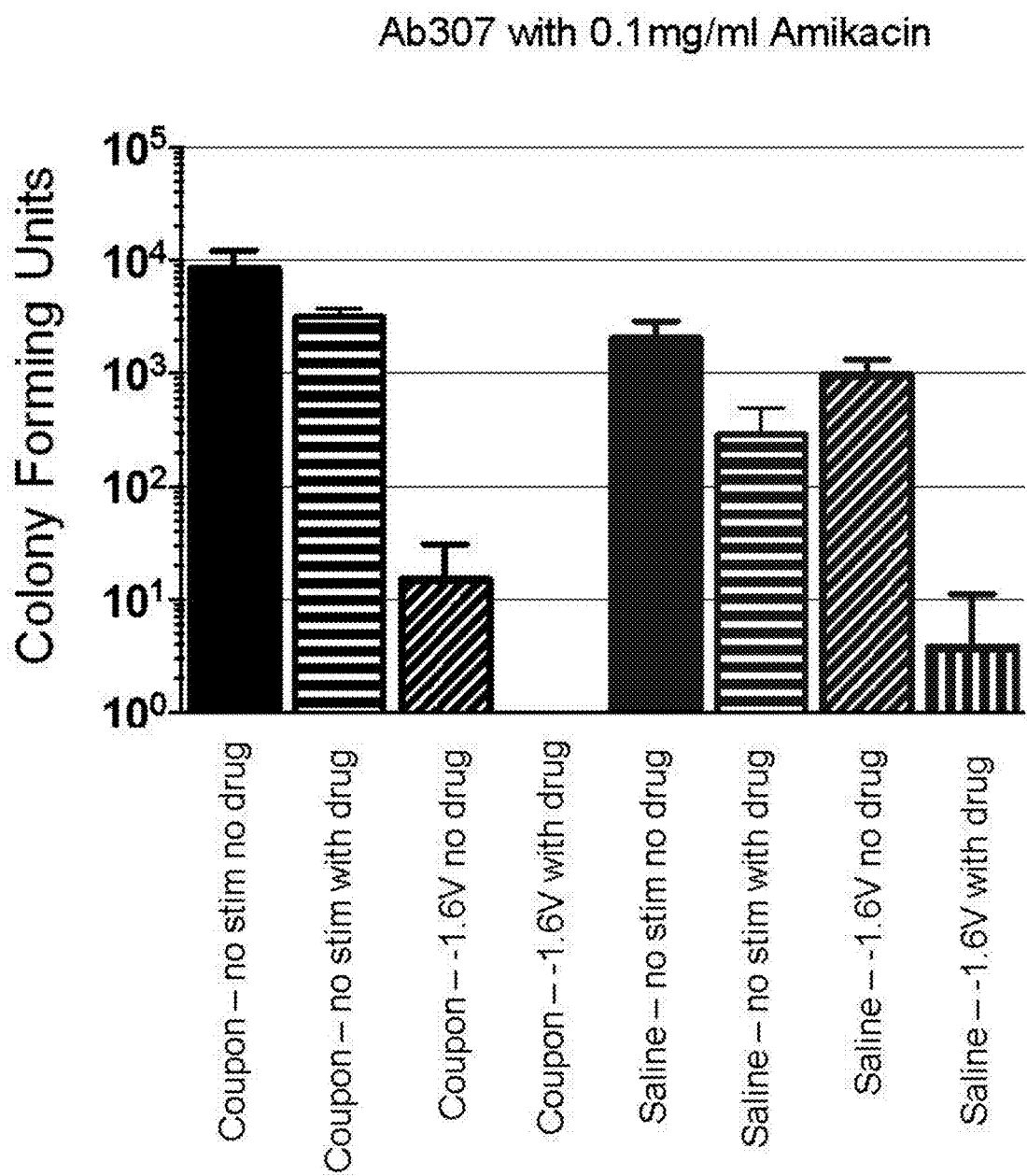
FIG. 7 is a chart showing reductions of CFUs at −1.6V in combination with an AM according to embodiments of the present invention.

In an effort to find a method to further reduce/eradicate the biofilm and planktonic CFUs we pursued experiments that introduced the use of antibiotics in combination with the electrical stimulation. In consultation with our collaborating infectious disease physician, we chose to utilize Amikacin as our antibiotic in the Ab307 experiments. We first had to characterize the effective dosing of Amikacin against Ab307 at a concentration of 10$^4$ CFUs. To do this we utilized both agar and broth dilution methods to determine the minimal inhibitory concentration (MIC) and the minimal bactericidal concentration (MBC). These standard clinical and laboratory methods determine the effectiveness of the antibiotic on planktonic bacteria only. It was determined that the MIC of Amikacin against 10$^4$ CFUs of Ab307 was 4 µg/mL while the MBC was 8 µg/mL. Knowing these standard lab concentrations for planktonic bacteria allowed us to start evaluating the dosing of Amikacin that is effective against 10$^4$ CFUs of Ab307 in biofilms. Previous literature suggests that the MIC for bacteria in a biofilm may be 500-5000 times the MIC for planktonic bacteria. We performed a series of titration experiments and determined that at a concentration of 1 mg/mL and above (≥250×MIC of planktonic) that Amikacin will completely eradicate a 10$^4$ CFU biofilm of Ab307. Starting with this dose as our upper limit we sought to identify an antimicrobial synergism such that utilization of electric stimulation may reduce the high dosing of Amikacin that is needed to eradicate biofilms. The data presented in FIG. 7 are the averaged coupon and saline CFUs from several experiments conducted at −1.6V stimulation for 1 hr either in the presence or absence of 0.1 mg/mL Amikacin. FIG. 7 shows a plot of average CFUs enumerated from the coupons and saline for experiments conducted with or without stimulation of −1.6V and with or without 0.1 mg/mL Amikacin.

As shown the coupon CFUs for each experimental condition were all significantly different from each other and zero CFUs were recovered from the coupon that received the −1.6V stimulation and exposure to Amikacin. The saline CFUs present in the −1.6V stimulation plus Amikacin group and the no stimulation with Amikacin group were each significantly different from all other groups. The saline CFUs from the stimulation alone group were similar to the unstimulated controls. These outcomes were notable because the synergistic antimicrobial effect of −1.6V stimulation in the presence of 0.1 mg/ml Amikacin on both biofilm and planktonic *A. baumannii* highlights the great potential this method has for possible clinical translation.

EXAMPLE 6

We have also performed experiments to assess the antimicrobial properties of constant cathodic voltage stimulation against preformed biofilms (18 hr incubation, ~10$^7$ CFUs) of Gram-positive MRSA (NRS70). The results of initial experiments performed at −1.7V and −1.8V for 1 hr are shown in FIGS. 11a-b. The compiled and averaged data is displayed in FIGS. 12a-c. Reductions in the mean CFUs enumerated from the coupons and saline were noted for the −1.7V and −1.8V stimulations as compared to the no stimulation controls. FIG. 11 shows plots of the experimental outcomes for constant cathodic potentials of −1.7V(a), −1.8V(b) applied for 1 hours to cpTi samples with preformed biofilms of Gram-positive MRSA (NRS70). Each plot contains the biofilm CFUs enumerated from the no stimulation controls and experimental stimulations. The inoculum (white) indicates the initial pre-stimulated CFUs contained on each cpTi coupon. Also present in each plot are the planktonic CFUs enumerated from the saline surrounding the no stimulation controls and the experimental stimulation conditions. The average cathodic current density associated with each channel during the applied voltages is also shown in all plots as blue bars with white slashes. The CFU axis is on the left while the current density axis is on the right. FIG. 12 shows plots of the average CFUs enumerated from the coupons (12a) and saline (12b) for each 1 hour stimulation condition. The average cathodic current density for each 1 hour stimulation condition is also shown in (12c).

EXAMPLE 7

Figure 13:
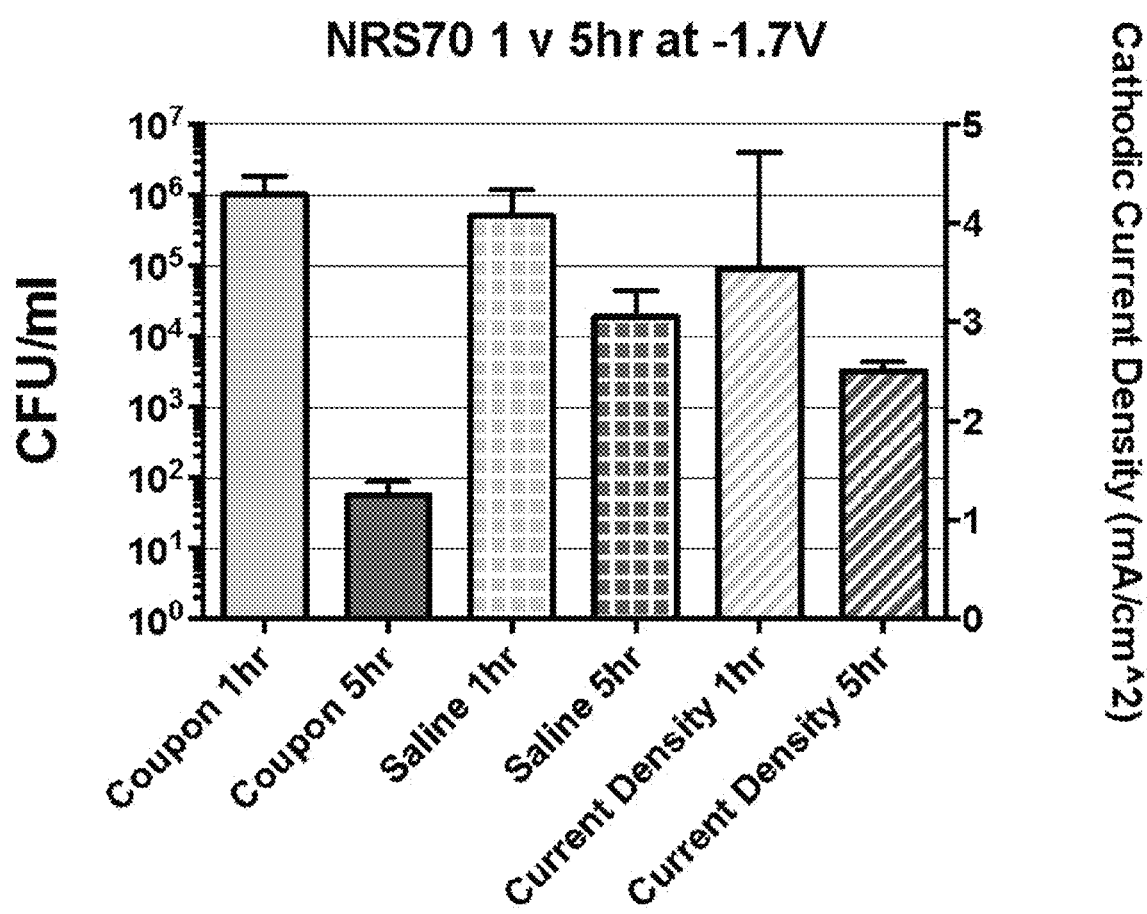
FIG. 13 is a chart showing reductions of CFUs at −1.7V for either 1 hr or 5 hrs according to embodiments of the present invention.

We subsequently performed a series of experiments in which −1.7V stimulation was delivered to cpTi samples with preformed NRS70 biofilms (18 hr incubation, ~$10^7$ CFUs) for either 1 hr or 5 hrs. The averaged outcomes (FIG. 13) showed that the increased 5 hr stimulation reduces the CFUs enumerated from the coupon and the saline as compared to the 1 hr stimulation time, but that the current density remains same. Therefore, increasing stimulation time is an effective means to reduce CFUs of both biofilm and planktonic NRS70. FIG. 13 shows a plot of the average CFUs enumerated from the cpTi coupons and the surrounding saline following −1.7V stimulation for 1 hour or 5 hours. Also shown is the average cathodic current density through the 1 hour or 5 hour stimulation period. The CFU axis is on the left while the current density axis is on the right.

EXAMPLE 8

Figure 14:
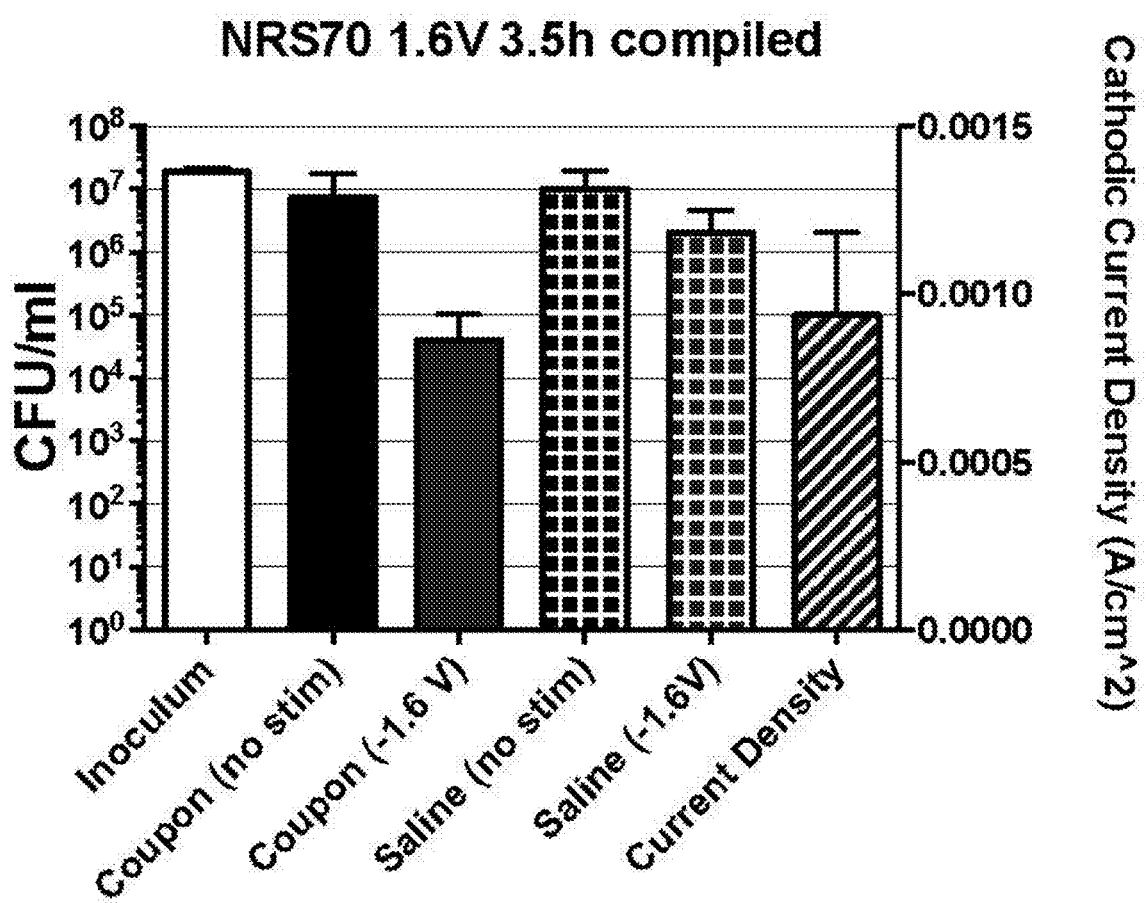
FIG. 14 is a chart showing a plot of average CFUs at −1.6V for 3.5 hours according to embodiments of the present invention.

We have also conducted experiments where −1.6V has been applied to NRS70 biofilms (18 hr incubation, ~$10^7$CFUs) for 3.5 hrs. The results (FIG. 14) show that this prolong stimulation reduces the mean CFUs enumerated from the coupon and saline as compared to the no stimulation controls. This again shows the utility of this constant cathodic voltage stimulation as an antimicrobial tool for cpTi implants. FIG. 14 shows a plot of the average CFUs enumerated from the cpTi coupons and the surrounding saline following −1.6V stimulation for 3.5 hours. Also shown is the average cathodic current density through 3.5 hour stimulation period. The CFU axis is on the left while the current density axis is on the right.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A method of treating a surface of an object, wherein the object is of such material that it can act as a working electrode, the method comprising:
   providing a reference electrode, a counter electrode, and the object acting as the working electrode;
   passing electrical current through the working and counter electrodes, wherein the current through the counter electrode is varied such that the electric potential of the working electrode is substantially constant relative to the electric potential of the reference electrode; and
   wherein the object is implantable or implanted.

2. The method of claim 1, wherein the step of passing electrical current through the working and counter electrodes is performed using a potentiostatic device.

3. The method of claim 2, wherein the potentiostatic device is a potentiostat.

4. The method of claim 1, further comprising the step of providing an antimicrobial agent to a region surrounding the object.

5. The method of claim 1, wherein the implantable or implanted object has an oxide layer on at least part of the surface of the object.

6. The method of claim 1, wherein the implantable or implanted object is at least partially made from titanium.

7. The method of claim 1, wherein the implantable or implanted object is at least partially made from stainless steel, cobalt, chromium, molybdenum or any combination thereof.

8. The method of claim 1, wherein the reference electrode is at least partially made from silver or silver chloride.

9. The method of claim 1, wherein the counter electrode is at least partially made from platinum, graphite, or carbonized silicone rubber.

10. The method of claim 1, wherein the passing of electrical current results in reducing or preventing the growth of microbes.

11. The method of claim 10, wherein the microbes are a part of a biofilm.

12. The method of claim 11, wherein the microbes are bacteria or fungi.

13. The method of claim 1, wherein the constant electric potential of the working electrode is selected from the range of about −0.5 to about −10.0 V with respect to the reference electrode.

14. A method of treating a surface of an object, wherein the object is of such material that it can act as a working electrode, the method comprising:
   providing a reference electrode, a counter electrode, and the object acting as the working electrode;
   passing electrical current through the working and counter electrodes, wherein the current through the counter electrode is varied such that the electric potential of the working electrode is substantially constant relative to the electric potential of the reference electrode; and
   wherein the passing of electrical current results in reducing or preventing the growth of microbes.

15. The method of claim 14, wherein the microbes are a part of a biofilm.

16. The method of claim 15, wherein the microbes are bacteria or fungi.

* * * * *

UNITED STATES PATENT AND TRADEMARK OFFICE
CERTIFICATE OF CORRECTION

| | | |
|---|---|---|
| PATENT NO. | : 9,616,142 B2 | Page 1 of 1 |
| APPLICATION NO. | : 14/540213 | |
| DATED | : April 11, 2017 | |
| INVENTOR(S) | : Ehrensberger et al. | |

It is certified that error appears in the above-identified patent and that said Letters Patent is hereby corrected as shown below:

In the Specification

Column 1, Lines 19–22 should read:
--This invention was made with government support under Grant No. W81XWH-10-1-0696 awarded by the US Army Medical Research and Material Command. The government has certain rights in the invention.--

Signed and Sealed this
Nineteenth Day of December, 2017

Joseph Matal
*Performing the Functions and Duties of the
Under Secretary of Commerce for Intellectual Property and
Director of the United States Patent and Trademark Office*